United States Patent [19]

Vogel

[11] 4,439,453

[45] Mar. 27, 1984

[54] DIRECTLY COMPRESSIBLE ACETAMINOPHEN GRANULATION

[75] Inventor: Stephen H. Vogel, Collinsville, Ill.

[73] Assignee: Monsanto Company, St. Louis, Mo.

[21] Appl. No.: 421,212

[22] Filed: Sep. 22, 1982

Related U.S. Application Data

[63] Continuation of Ser. No. 219,290, Dec. 22, 1980, abandoned.

[51] Int. Cl.³ .......................... A61K 9/16; A61K 9/34; A61K 9/60; A61K 9/62
[52] U.S. Cl. ...................................... 424/324; 424/34; 424/35; 424/361
[58] Field of Search .................... 424/34, 35, 324, 361

[56] References Cited

U.S. PATENT DOCUMENTS 4,097,606 6/1978 Chavkin ............................ 424/324

OTHER PUBLICATIONS

Gissinger, Labo.-Pharma Problems & Tech., vol. 28, Jan. 1980, pp. 27-31.
Bhatia, Drug & Cos. Ind., Apr. 1978, pp. 38, 39, 42, 44, 52, 171-175.
Nautamlal, Dissertation Abs. Int., vol. 40, No. 11, May 1980, pp. 5214B-5215B.

*Primary Examiner*—Stanley J. Friedman
*Attorney, Agent, or Firm*—Jon H. Beusen; J. C. Logomasini; A. H. Cole

[57] ABSTRACT

A free flowing granulation, comprising a high concentration of acetaminophen and a low level of excipient, including ground cross-linked sodium carboxymethylcellulose fiber, allows the manufacture of analgesic tablets by direct compression. The method provides improvements in manufacturing economics and tablet properties.

15 Claims, No Drawings

DIRECTLY COMPRESSIBLE ACETAMINOPHEN GRANULATION

This is a continuation of application Ser. No. 219,290, filed Dec. 22, 1980, now abandoned.

BACKGROUND OF THE INVENTION

This invention relates to the preparation of tablets comprising acetaminophen. In general, there are four principle methods widely used in the United States for tablet manufacture. The four methods are:

Direct Compression—In this method, all required tableting aids are incorporated in a free flowing granulation as supplied by the bulk analgesic manufacturer. The granulation requires no pre-processing, or blending with additional aids, and is charged directly to a tableting press. This method is used extensively in the manufacture of generic aspirin tablets.

Dry Powder Blend—In this method all required tableting aids are blended with crystal grade acetaminophen or aspirin. The blend is then charged directly to a tableting press. Gelatin or polyvinylpyrrolidone coated acetaminophen powder is sometimes used in place of crystal grade acetaminophen.

Pre-Compressed Dry Powder Blend—In this method the dry powder blend containing all required tableting aids is pre-compressed either by roll compaction or slugging. Roll compaction is the most popular method of preparing granulated aspirin. A homogenous blend of aspirin and starch is roll compacted, milled, sifted and drummed. The granulated product is charged directly to a tableting press.

Wet Granulation—This is the most popular method of granulating acetaminophen. In this method acetaminophen crystal or powder is blended with intragranular excipients, then wetted to a moist powder consistency with an aqueous binder solution. In some cases the powder is wetted to a dough consistency and forced through a 10–14 mesh screen. The wetted mass is then dried by conventional means, milled, sifted, and blended with extragranular excipients and lubricant. This mixture is then fed to a tableting press.

Acetaminophen is not ordinarily amenable to tableting by the same methods as aspirin. These materials have significantly different properties. Thus, crystalline aspirin is easily tableted, since the crystals are quite soft and exhibit good plasticity/elasticity when compacted to tablets. Further, cohesive/adhesive bonding within the aspirin tablet is strong and the aspirin, itself, provides good lubricity to the formula. Accordingly, no lubricant is necessary in the formula used for aspirin tableting. In contrast, acetaminophen crystals are very hard and brittle and fracture very easily. The crystals have essentially no plasticity/elasticity and can be tableted by the normal aspirin tableting methods only by using high levels of excipients and large crystalline grade acetaminophen. Furthermore, at least 25% or more excipients are required in addition to high levels of lubricant. The large acetaminophen crystals have the disadvantage of being slowly dissolved in the body and require additional tableting aids to increase the rate of dissolution.

Accordingly, acetaminophen has been preferably tableted using the wet granulation method since the direct compression method, the dry powder blending method and the pre-compression method have not been shown to be amenable in acetaminophen tableting for the reasons noted above.

The direct compression method of preparing tablets would be the method of choice for preparing acetaminophen tablets if a formulation comprising acetaminophen could be prepared which would allow the use of such method. Accordingly, there is a need for an acetaminophen formulation containing all required tableting aids which may be used in direct compression tableting.

SUMMARY OF THE INVENTION

It is an object of this invention to provide a formulation comprising acetaminophen which is directly compressible to tablets.

It is a further object of this invention to provide an acetaminophen tablet which is prepared by a direct compression method.

The above objects of this invention are achieved by the process and formulation of the present invention, whereby an acetaminophen formulation having a low excipient level is provided which thereby allows economics in manufacture, because of the high cost of excipients, and the ability to prepare a smaller tablet having the same dosage of acetaminophen as larger tablets prepared by other methods. Further, the costly and tedious process of wet granulating is eliminated.

Although direct compression aspirin granulation is extensively used to prepare aspirin tablets, a similar formula and granulating process are not directly convertible to granulating acetaminophen because of the difference in characteristics between aspirin and acetaminophen. The present invention describes a formula and process which affords manufacture of direct compression acetaminophen granulation having similar excipient level and tableting characteristics as direct compression aspirin granulation. Excellent quality acetaminophen tablets having a high concentration of acetaminophen are attained by the direct compression method. Further, the granulation and tablets afforded by this invention are stable and non-pinking. The granulation is tabletable at a wide range of pressures providing tablets having remarkably rapid disintegration and dissolution features.

The uniqueness of the acetaminophen granulations of the present invention is due to the following considerations: (1) all excipients are incorporated in the granulation. No further addition of excipients is necessary for tableting. (2) the granulation contains a high, i.e. 80–90 wt. %, concentration of active analgesic agent, i.e. acetaminophen and (3) the granulation requires no pre-processing prior to tableting.

In general, the method of preparing the acetaminophen granulation of the invention comprises charging acetaminophen powder and other ingredients to be used in the tablet to a fluidizer, fluidizing the mixture with warm air while spraying the mixture with an aqueous starch slurry, drying the mixture, adding lubricant and mixing the ingredients to uniformity.

PREFERRED EMBODIMENTS OF THE INVENTION

In accordance with the present invention, it has been found that an acetaminophen formulation containing ground cross-linked sodium carboxymethylcellulose (NaCMC) fiber allows tableting of the acetaminophen formulation by the direct compression method, a method which has heretofore been unavailable for the tableting of acetaminophen formulations. The formulation comprising acetaminophen and ground NaCMC fiber provides superior quality tablets with respect to friability, dissolution, disintegration and tablet aesthetics.

Typically, prior acetaminophen granulations used for preparing tablets by the wet granulation method contained approximately 25-40% excipients. Commonly used excipients include binders such as gelatin, polyvinylpyrrolidone, and gelatinized starch, disintegrants such as corn starch and microcrystalline cellulose, glidants such as silica, talc, and corn starch, and lubricants such as stearic acid and stearate salts, e.g. magnesium stearate.

In contrast to the prior methods of tableting acetaminophen granulations, the process and granulation of the present invention allows the preparation of acetaminophen tablets containing 80-90% acetaminophen.

The unique qualities of the granulation of the present invention are attributable to the use of ground NaCMC fiber during the fluidized bed granulation, thereby allowing the higher percentages of acetaminophen in the granulation and still achieving high quality tablets.

In general, the granulations of the present invention comprise from about 80 to about 90% by weight acetaminophen, from about 0.1 to about 5.0% by weight ground NaCMC fiber, from about 1.0 to about 15.0% by weight pregelatinized starch, from about 0.1 to about 2.0% by weight lubricant, e.g. stearic acid or magnesium stearate. Alternative or additional excipients may include a binder, e.g. purified wood fiber; a disintegrant, e.g. sodium starch glycolate; an antioxidant, e.g. sodium metabisulfite; a preservative, e.g. propylparaben; a surfactant, e.g. alkali metal salts of high molecular weight alkyl sulfates or sulfonates and similar materials of like nature.

A typical preferred formula useful for granulation in accordance with the present invention, its method of preparation and the properties of the tablets obtained thereby as compared to commercial tablets are set forth in the following example and Table 1.

EXAMPLE

The following formula is utilized in this example:

TABLE 1

| Ingredient | Weight % |
|---|---|
| Milled Acetaminophen | 90.0 |
| Ground NaCMC Fiber | 3.50 |
| Pregelatinized Starch | 6.00 |
| Stearic Acid | 0.50 |

The above formulation is granulated in a fluidized bed granulator. The granulating conditions utilizing the formula are as follows:

6300 grams of milled acetaminophen and 245 grams ground NaCMC fiber are charged to the granulator and fluidized for about 2 to 5 minutes in order to homogenize the ingredients. A dispersion is then prepared utilizing 420 grams pregelatinized starch in 5,580 grams water via vigorous agitation. While mixing, the suspension is warmed to about 85° C. to effect gelling. The mixture is cooled and maintained at 60°-70° C. Agitation is maintained to avoid film formation on the surface. Just prior to use, 1.6 grams sodium metabisulfite dissolved in 50 ml water is introduced and mixed into the starch suspension. The dispersion is atomized onto the fluidized acetaminophen/ground NaCMC fiber over a period of 30-90 minutes under typical granulating conditions of air flow rate, temperature and spray nozzle parameters. When binder addition is completed, the batch is dried by continued fluidization with warm air to a moisture level of 0.7 to 1.5%. Magnesium stearate acid is added and blended into the product by fluidization for 1 to 5 minutes with ambient temperature air.

Although a 10% excipient level is shown in the above example, excipient levels of up to 20% and even higher, e.g. 25-40%, can be selected so long as ground NaCMC fiber is present in a range of about 0.1 to about 5.0% by weight. Other tableting aids and concentrations thereof besides those listed in the example can also be selected. Other acceptable binder solutions which can be used are solutions of gelatin, polyvinylpyrrolidone, polyethylene glycol or mixtures thereof separately or admixed with gelatinous starch or other binders.

I claim:

1. A directly compressible analgesic granulation comprising from about 80% to about 90% by weight acetaminophen, from about 0.1% to about 5.0% by weight ground crosslinked sodium carboxymethylcellulose fiber, from about 1.0% to about 15.0% binder and from about 0.1% to about 2.0% by weight lubricant.

2. Granulation of claim 1 which contains about 80% by weight acetaminophen.

3. Granulation of claim 1 which contains about 85% by weight acetaminophen.

4. Granulation of claim 1 which contains about 90% by weight acetaminophen.

5. Granulation of claim 1 which contains about 3.5% by weight cross-linked sodium carboxymethylcellulose fiber.

6. Granulation of claim 1 wherein said binder is pregelatinized starch.

7. Granulation of claim 6 wherein said starch is present in an amount of about 6% by weight.

8. Granulation of claim 1 wherein said lubricant is selected from the group consisting of stearic acid and magnesium stearate.

9. Granulation of claim 8 wherein said lubricant is present in an amount of about 0.5% by weight.

10. A directly compressible analgesic granulation comprising about 90% by weight acetaminophen, about 3.5% by weight ground cross-linked sodium carboxymethylcellulose, about 6% by weight pregelatinized starch and about 0.5% stearic acid.

11. An analgesic tablet comprising the granulation of claim 1.

12. An analgesic tablet comprising the granulation of claim 10.

13. A method of preparing an analgesic granulation which comprises admixing acetaminophen and ground cross-linked sodium carboxymethylcellulose fiber in a granulator and fluidizing same, forming a dispersion of binder in water and atomizing said dispersion onto said fluidized admixture, drying same by continued fluidization in the presence of heated air and adding thereto a lubricant.

14. Method of claim 13 wherein said binder is pregelatinized starch.

15. Method of claim 1 wherein said lubricant is stearic acid.

* * * * *

UNITED STATES PATENT AND TRADEMARK OFFICE
CERTIFICATE OF CORRECTION

PATENT NO. : 4,439,453
DATED : March 27, 1984
INVENTOR(S) : Steve H. Vogel

It is certified that error appears in the above-identified patent and that said Letters Patent is hereby corrected as shown below:

Column 4, line 8 should read:

-- rate or stearic acid is added and blended into the product by fluid- --.

Signed and Sealed this

Sixteenth Day of October 1984

[SEAL]

Attest:

GERALD J. MOSSINGHOFF

Attesting Officer

Commissioner of Patents and Trademarks